United States Patent [19]
Perlman

[11] Patent Number: 5,061,621
[45] Date of Patent: Oct. 29, 1991

[54] REPLICA PLATING DEVICE WITH AN INTEGRAL MARKING ELEMENT

[75] Inventor: Daniel Perlman, Arlington, Mass.

[73] Assignee: Brandeis University, Waltham, Mass.

[21] Appl. No.: 369,753

[22] Filed: Jun. 22, 1989

[51] Int. Cl.[5] .......................... C12Q 1/24; C12M 1/26
[52] U.S. Cl. ..................................... 435/30; 435/287; 435/292
[58] Field of Search .................. 435/292, 294, 240.23, 435/240.243, 243, 287, 30, 300, 298

[56] References Cited

U.S. PATENT DOCUMENTS

| | | | |
|---|---|---|---|
| 2,361,992 | 11/1944 | Cantor | 435/298 |
| 3,875,015 | 4/1975 | Wadley et al. | 435/292 |
| 4,596,773 | 6/1986 | Wheeler, Jr. | 435/300 |
| 4,634,676 | 1/1987 | Sapatino | 435/294 |
| 4,659,672 | 4/1987 | Provonchee et al. | 435/287 |
| 4,717,667 | 1/1988 | Provonchee | 435/292 |

FOREIGN PATENT DOCUMENTS

240908 11/1986 Denmark ............................ 435/292

OTHER PUBLICATIONS

Lederberg et al., "Replica Plating and Indirect Selection of Bacterial Mutants", Dept. of Genetics, Wis., p. 399, (1952).
Curtis et al., "The RepliPlate TM Colony Transfer Pad: A New Device for Replicating Microbial Colonies", Biotechniques, p. 153, (1983).
Maniatis et al., "Replica Filters", Molecular Cloning, A Laboratory Manual Cold Spring Harbor Laboratory, 1982.
FMC Corporation, Advertisement, Jan. 1987.
Linkkila et al., "Accurate Replication of Microbial Colonies Using a New Replica Plating Device", Presented at the 90th Annual Meeting of The American Society for Microbiology, Anaheim, Calif., May 1990.

*Primary Examiner*—David L. Lacey
*Assistant Examiner*—William Chan
*Attorney, Agent, or Firm*—Lyon & Lyon

[57] ABSTRACT

Device for replica plating of living cells. The device includes a rigid base having a side wall connecting a first upper surface and first lower surface, and a water absorbing fabric free from dye and preservatives having a second upper surface and a second lower surface. The second lower surface is fixedly bonded to the first upper surface in a manner which prevents any horizontal or vertical movement of the fabric which would cause inaccurate transfer of the cells by the device. The base further includes an adhesive tab positioned on the first lower surface. The tab is configured and arranged to fixedly secure the base to a flat surface and thereby fixedly secure the fabric in a positioned raised above the flat surface and accessible for replica plating of the cells. The device may also contain integral marking element and bumper guards.

26 Claims, 1 Drawing Sheet

REPLICA PLATING DEVICE WITH AN INTEGRAL MARKING ELEMENT

BACKGROUND OF THE INVENTION

Replica plating of cellular colonies is a widely used technique in molecular biology and genetics. The process of replica plating involves a printing-like transfer of a set of colonies from one culturing surface (such as a gel medium in a Petri dish) to another culturing surface or surfaces. The transfer process is performed by contacting colonies with a sterile transfer pad to which some of the cells from each colony adhere, and then contact printing these cells onto one or more additional culturing surfaces to deposit some of the cells. This technique was originally described by Lederberg et al., J. Bacteriology 63:399 (1952) where 12 cm squares were cut from velveteen yardage and a square placed nap up on a cylindrical wood or cork support, and held firmly in place by a metal flange or hoop pushed over the fabric and around the rim of the support. An agar plate carrying the initial colonies was inverted onto the fabric with slight digital pressure to transfer the cells from the culturing surface. The imprinted fabric provided the pattern for transferring replica inoccula to subsequent plates impressed in the same way. This technique is still commonly used today with the fabric squares being washed, sterilized, and used repeatedly. When the fabric squares are first prepared from new fabric, they must be washed one or more times to remove chemicals within them that are inhibitory to colony growth.

Curtis et al., Biotechniques 152 (March/April 1985) describe a replica plating colony transfer pad. They state that velvet is of limited use for such a pad because its preparation is labor intensive, and the quality and quantity of replicates that can be obtained is restricted. They mention that a number of other materials, such as nitrocellulose and nylon membranes, are now commonly used, and that each have positive and negative attributes. Toothpicks and microloops also continue to be used for transfer of individual colonies. The authors state that a convenient, ready to use device is provided consisting of a laminated polyurethane foam pad coated with a water absorptive film.

Provonchee, U.S. Pat. No. 4,717,667, describes a replica plating device having a rigid layer, and a transfer surface formed from an open cell flexible foam, including a hydrophilic layer. Provonchee states that a resilient backing layer is one of the essential elements of the device. This backing layer is resilient to deform at least generally in response to the surface contour of the growth medium on which the cells to be transferred are supported. Provonchee states that the conventional velvet pad has certain limitations. The velvet pad is essentially a series of needle tips in a fixed array, with the spaces between the needle tips serving as a collector of moisture which the pad soaks up when contacted with a growth medium. It is necessary that such moisture be accommodated, lest lateral smearing of replicate colonies result. However, Provonchee states that the colony transfer surface of his device may be chosen from conventional cut pile velvet, which may be bonded to the resilient backing layer with a water-based latex binder.

Maniatis et al., Molecular Cloning and Laboratory Manual, Cold Spring Harbor, 1982, on pages 304–306 describe use of a conventional replica plating tool, having velvet at its transfer surface, for replica plating phase particles to nitrocellulose paper.

Sapatino, U.S. Pat. No. 4,634,676, describes a replica plating device having a hooked skirt extending over the rim of a culture container and downwardly over this rim to prevent excessive movement of the pressing surface within the container. This skirt does not appear to prevent contact between the side wall of the replica plating device and the inside wall of the culture dish container. The device includes a compressible material, for example, velvet, which serves to cushion the pressing effect of the replica plating device against the cells and culture medium during use. This compressible material may be adhesively attached to the exterior surface of the bottom wall of the replica plating device.

SUMMARY OF THE INVENTION

The invention features a device for replica plating of living cells. Considering the device oriented with its cell transfer surface face up, the device includes a rigid supporting base having a first upper surface and first lower surface, these surfaces being connected by a sidewall, and a water absorbing fabric free from dye and preservatives, this fabric having a second upper surface and a second lower surface. The second lower surface is fixedly bonded (i.e., attached) to the first upper surface in a manner which prevents any horizontal or vertical movement of the fabric which would cause inaccurate transfer of the cells by the device. The base further includes an adhesive tab positioned on the first lower surface. The tab is configured and arranged to fixedly secure the base to a flat working surface and thereby fixedly secure the fabric in a position raised above the flat surface and accessible for replica plating of the cells.

The device may be provided with at least one integral extension structure which serves as a marking instrument or marking means, and is positioned on or near the sidewall or perimeter of the device, and protrudes above the second upper surface. The protruding marker is configured and positioned to assure that each gel culture surface, contacted by the cell transfer surface of the device, automatically and simultaneously receives a visible permanent impression mark. Such a reference mark made on each of a series of growth medium surfaces assures that the pattern of colonies on one such surface can be visually aligned and compared with the pattern of replicated colonies on another surface.

By replica plating of living cells is meant the procedure for forming a copy of colonies of living cells present on a growth medium. These cells may be procaryotic or eucaryotic cells, or viral particles.

In preferred embodiments, the base includes a set of bumper guards positioned between the first upper surface and the first lower surface on the side wall of the base. The guards are configured and arranged to prevent significant contact of the fabric and the side wall of the device with the inside wall of a culture dish or plate holding the cells to be replica plated, e.g., the guards include three or more elongated ridges projecting from the side wall of the base; the device also includes a water absorbing material positioned between and fixedly bonded to the first upper surface and the second lower surface, e.g., filter paper; the fabric is a loom stage woven fabric material, most preferably a loom stage woven 100% cotton pile fabric, such fabric, which has been warp cut, sheared, boiled-off and framed is particularly suited to this invention; the base is cylindrical and the fabric covers the first upper surface and does not extend outward beyond the outer circumference of the first upper surface; the base is formed of biodegradable plastic; and a cover is removably positioned over the fabric in a manner which maintains the sterility of the fabric.

In a related aspect, the invention features a method for replica plating living cells. The method includes providing a device adapted for replica plating of the cells, including a rigid base having a first upper surface and a first lower surface connected by a cylindrical sidewall, and a water absorbing fabric free from dye and preservatives having a second upper surface and a second lower surface. The second lower surface is fixedly bonded to the first upper surface in a manner which prevents any horizontal or vertical movement of the fabric which would cause inaccurate transfer of the cells by the device. The base further includes an adhesive tab positioned on the first lower surface, the tab being configured and arranged to fixedly secure the base to a flat working surface, such as a laboratory bench, and thereby fixedly secure the fabric in a position raised above the flat working surface and accessible for replica plating of the cells. The method further includes positioning the device on a flat working surface with the tab fixedly secured to the working surface; placing the colonies of cells in contact with the second upper surface to cause some of the cells to be transferred to the second upper surface; and subsequently placing a plate in contact with the second upper surface to cause some of the cells to be transferred to the plate.

In related methods, the fabric is a loom stage woven pile fabric; and an integral reference marking means is provided to cause reference marks to be produced in cell culture surfaces, simultaneously with colony transfer using a replica plating device.

Devices of this invention are advantageous over those in the prior art in that they maximize the rate at which the replica plating transfer fabric can absorb moisture from a cell culture surface, and thus enhance the quality and accuracy of the transfer, and maximize the number of colony transfers which can be carried out. The adhesive tab introduced on the first lower surface of the device anchors the device to prevent inadvertent movement during transfers which can cause colony smearing. The fabric preferably used in this device is a loom stage woven pile fabric material having substantially no dyes or preservatives which inhibit the growth of living cells, while also providing a large number of needle-like projections to allow accurate cellular replica formation. Such material can be provided with a relatively shallow pile of needles to allow formation of a greater number of faithful replicates. This material is rigidly adhered to a rigid base to prevent any significant movement either horizontally or vertically of the fabric surface, and thus provides an enhanced quality of replica plates. Replicas produced with this device are less likely to be smeared, and there is a reduced chance for loss of small sized colonies within the fabric. Thus, devices of this invention improve the quality and quantity of cell replicas that can be obtained in each replica plating procedure.

In the most preferred embodiments of the present invention, the rate of moisture transmission into and through the colony transfer pad, as moisture is expressed from the culturing surface during replica plating, is maximized by provision of not only a water absorbing fabric, but also of a water absorbing material positioned below that fabric. Such extra water absorbing material increases the capacity of the transfer path for water over that of a fabric surface alone. I have found that, because culture medium (e.g., agar) surfaces are essentially flat as they solidify in a dish (except for a meniscus edge of the medium), provision of an essentially rigid non-flexing transfer pad (combined with rapid water transfer through the transfer pad into a sublayer) provides a higher quality of serial colony transfer than provision of high compliance or resilient foam pads intended to follow any irregularities in an agar surface.

To avoid contact with the raised meniscus edge of the medium, bumper guards are provided in the device of the invention. These guards also prevent contact with moisture often encountered at the meniscus edge, thereby preventing excessive hydration of the fabric of the device, and thus enhancing the quality of replica transfers. These guards are also designed to keep the fabric away from the inside wall of the dish where additional moisture frequently accummulates. Such moisture makes production of useful replicas difficult if it contacts the fabric. These bumper guards help to reduce moisture-related colony smearinq caused by accidental contact with this inside wall. In addition, such guards can be readily modified to provide useful marking means which aid in orientation of replicas of the original colony containing plate.

Other features and advantages of the invention will be apparent from the following description of the preferred embodiments thereof, and from the claims.

DESCRIPTION OF THE PREFERRED EMBODIMENTS

The drawings will first briefly be described.

Drawings

Figure 1:
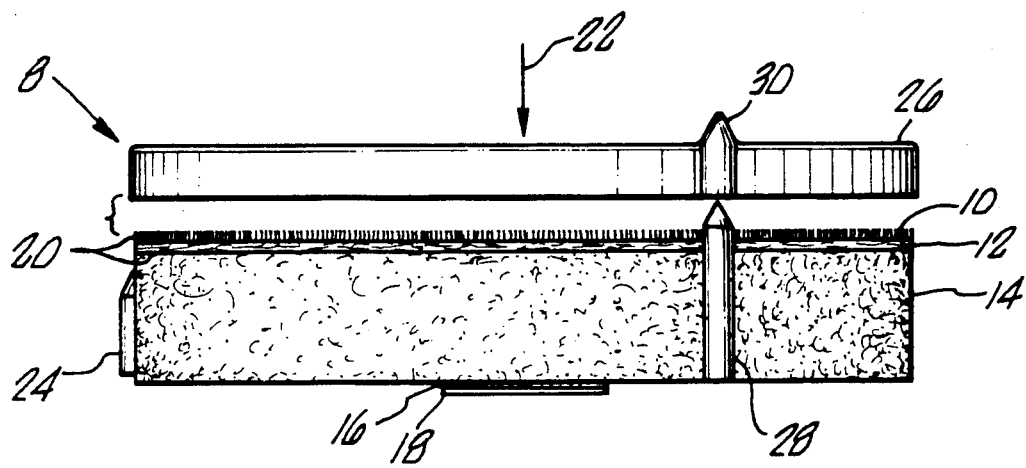
Figure 2:
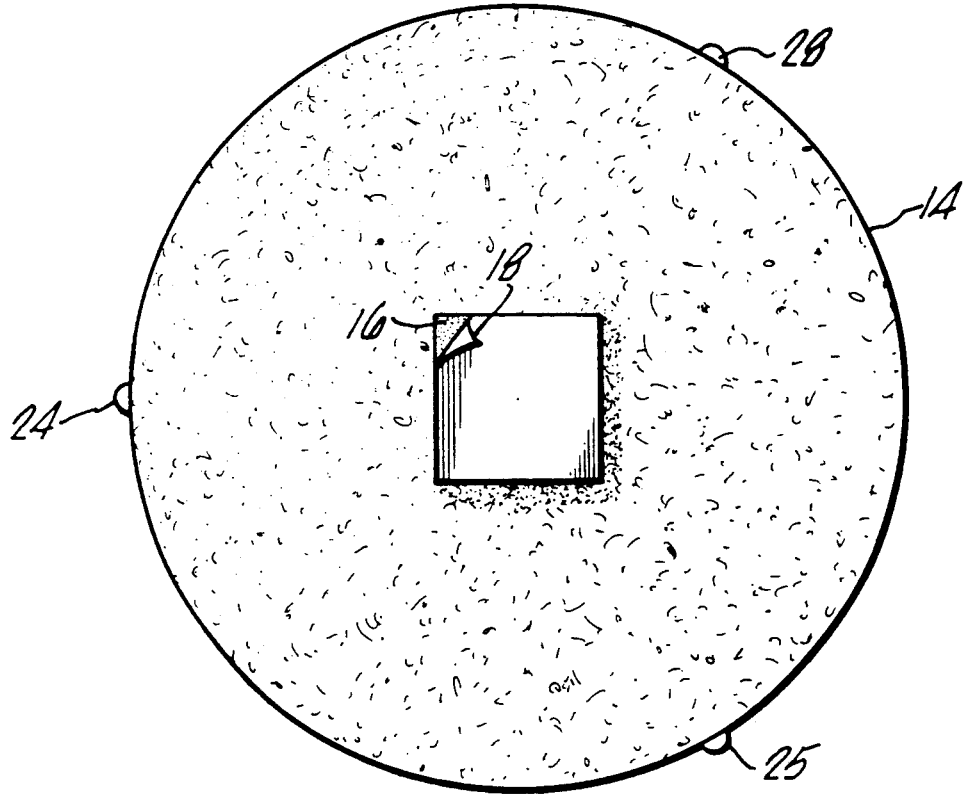

FIG. 1 is a side view of a replica plating device; and FIG. 2 is a bottom view of the device.

Structure

Referring to the FIGS., briefly, device 8 includes an undyed and unpreserved loom stage woven pile fabric colony transfer layer 10 (preferably sheared, singed, boiled and framed 100% cotton pile fabric) having a pile thickness selected in the range of between 0.5 and 2.0 mm, laminated with an absorbent blotting material sublayer 12 (preferably cellulose fiber) approximately 0.5–3.0 mm thick, and a rigid base 14 approximately 1.5 cm thick (e.g., styrofoam). An adhesive strip 16 with a peelable non-sticking cover paper 18 is attached to the bottom of the base. A latex-based laminating adhesive 20 is applied in a discontinuous pattern between layers 10, 12 and 14 to provide a firm bonding of these layers. A laminating adhesive covering of less than 20% of the surface area of the layers causes no significant decrease in the rate of, or capacity for, water transported from the surface of layer 10 into the absorbent layer 12. Three raised spacers or bumper guards 24, 25, 28 are provided, spaced 120° apart around the circumference of the base. These guards prevent contact of the colony transfer layer with the inside wall and meniscus edge of the culture medium in a culture dish. One of these guards 28 is elonqated into a fin-shape to act as a marking means, extending approximately 1/16"–⅛" above surface layer 10. The marking means leaves an impression, i.e., a reference mark, on a cell culture surface when contacted by device 8. A thin plastic cover 26, which protects layer 10, is included so that, once sterilized, the device is easily handled without contaminating layer 10, and can furthermore be pressed down (as shown by arrow 22 direction) to anchor it (by adhesive strip 16) on a laboratory bench. This cover is provided with a detent 30 to accommodate marking means 28.

The rapidly water-transmitting and air permeable surface layer 10 is formed from a pile-type material for colony transfers consisting of closely spaced threads typically oriented perpendicular to the surface of the material. This material is immobilized on, and bonded to, a substantially rigid or rigidly supported highly absorbent sublayer or backing material 12. The sublayer, whose affinity and capacity for water is preferably equal to or greater than that of the colony transfer layer material, may be homogeneous in composition or alternatively formed from a composite or laminated material. For example, a homogeneous absorbent layer may be a thick pressed-cellulose absorbent paper fiber pad. Other suitable absorbent materials include porous paper, woven and non-woven fabrics, natural and synthetic hydrocolloids, and mixtures thereof. Alternatively, as a laminated structure, the backing sublayer may be formed of a thinner but highly absorbent layer, pad or blotting filter (such as Whatman 3 MM paper or BRL DNA Blotting Pad) backed by a rigid non absorbent plastic sheet material (such as polystyrene sheet approximately 30–60 mils thick) or a thicker non-absorbent rigid foam base (such as that made of styrofoam). The thickness of such a base, contributing to the overall thickness of the replica-plating device, is chosen to allow the device's transfer surface to make physical contact with a cell culture medium, such as agar medium whose surface may be recessed in a dish, e.q., a Petri dish. A rigid base 14, having a thickness of approximately 1-2 cm is generally sufficient in thickness to allow such contact between the device and the culture medium.

The nap or pile-type material 10 is uniformly anchored and bonded to the rigid underlying absorbent support surface or backing 12. By immobilizing and bonding the flexible nap or pile-type transfer surface to its backing, the freedom of the velvet nap material to flex open and closed (mechanical "working") is minimized. Such mechanical working occurs when a velvet material held only by an outer circular flange, hoop, or ring, separates from the agar surface during replica plating. The center of the velvet, being last to break contact with the agar surface tends to be pulled away from its wooden or cork support. Such movement of the velvet pile creates movement of cell colonies on top of, and among the threads of the nap or pile, tending to distort and blur the original imprint of cells on the velvet. This distortion process is repeated, and accuracy diminishes with each contact with agar during serial replica-plating.

The pile or nap-type colony transfer surface is placed against a highly absorbent sublayer or backing material 12, having ample capacity to hold excess moisture from multiple serial transfer operations on nutrient medium. This permits the selection of a colony transfer surface which, while absorbing water very rapidly, may itself have a limited total capacity for water. Thus, instead of using a loose deep pile pad it is preferred to use a very dense shallow pile fabric such as 0.5 mm thick loom stage woven cotton pile fabric exhibiting very rapid capillary transmission of water. Such material, bonded to an appropriate rigid absorbent material, exhibits minimal mechanical movement or bending of the short needle-like pile threads during replica plating on culturing surfaces. With the absorbent material present, approximately 10–25 serial replica transfers of colonies are readily carried out with high reproducibility and accuracy. Without the absorbent sublayer present to remove excess moisture accumulated during serial replica-transfers, fewer accurate replicas can be produced (typically less than 10).

The various components of this device will now be discussed in detail.

Loom stage fabric

It has been determined that undyed and unpreserved 100% cotton woven pile fabric is a replica plating transfer material superior to those materials previously used in the prior art, including standard velvet material. This is because it is non-toxic and rapidly transmits moisture through its pile, and because it picks up and deposits many different species of microorganisms cultured on nutrient surfaces, such as nutrient agar. A dense material with a high thread count (typically about 1000–2000 pile threads per square inch) and a short pile (less than 1 mm length threads) is a preferred material. Commercially available cotton velvet and velveteen materials (Majestic Mills Inc., New York, NY) contain one or more substances which are toxic to and typically interfere with or reduce cell growth rate following replica-plating. It is likely that either leachable color dyes and-/or traces of preservatives (such as formaldehyde) in the fabric are harmful to such cell growth One or two successive laundry washes of the fabric typically eliminate these toxic components before sterilizing and packaging them for the first time. This laundry treatment is inconvenient and costly in commercial manufacture processing. Prior to dye color addition and subsequent chemical preservative additions, pile fabric precursors to commercial velveteen are manufactured, termed "first loom stage" pile fabric, which is produced as the material emerges from the weaving loom; and second stage or "boiled loom fabric" material, which is whitish in appearance and is produced from first loom stage by shearing to a constant thickness and boiling in water. Both the first and the second loom stage materials have tested non-toxic in cell culturing experiments. The second loom stage material is hydrophilic, and more water absorbent than the first stage material. It is believed that the boiling step eliminates potato starch which otherwise limits the hydrophilic nature of cotton. The boiled loom stage cotton pile fabric is a preferred material for use in colony transfer devices.

A variety of velvet and velveteen fabrics which are currently washed, sterilized and recycled in replica plating operations are expensive and range in price from $7.00 to $20.00 per square yard. In the preferred use of the present device, it is convenient to discard the device after use. To this end, the device is economically designed. First, the surface area of material required in the flat disc format of the present invention is 2–3 fold less than use of conventional velvet fabric which generously overlaps a wood or cork support so that a metal flange can be slipped down over the fabric to anchor it. Second, since the present invention incorporates an absorbent material to hold water behind the pile type transfer layer, utilization of a relatively thin and less costly material is possible. Further, undyed and unpreserved pile fabric precursors to velveteen material are typically 2–3 fold less expensive than the highly water-absorbent upholstery velvet previously used.

Bumper guards

It is important to prevent contact of a replica plating device with moisture droplets in a cell culture dish. Water condensation is often found around the inner wall of a cell culture dish, and physical contact with this wall allows transmission of the moisture to the adjoining surface of the growth medium where smearing of colonies on both the growth medium surface and on the device's transfer surface may occur. In addition, a raised meniscus of agar (or other solid nutrient medium) is always found around the inner circumference of the growth medium-containing dish. If the transfer device is inadvertently placed up against the side wall of the dish, the raised meniscus interferes with flat contact between the transfer device and the nutrient surface. This interference decreases the accuracy and quality of replicas produced during the replica plating operation.

To solve the above problem, a spacing means for separating the wall of the transfer device from the inside wall of the dish was constructed. This spacing means can assume one of several different geometries. In one version, three evenly spaced bumpers, in the form of small raised ridges or protruding knobs, are placed at intervals of 120° of arc relative to one another around the circumference of the device. These protuberances are typically between approximately 1/16 and ⅛" in depth. By appropriately separating the side of the transfer device from the inner wall, these spacers also prevent the colony transfer surface of the device from resting on the meniscus of the nutrient surface abutting the inner wall of the Petri dish. (It is estimated that the meniscus typically extends less than ⅛" from the sidewall of the dish).

In another embodiment of the spacer means, the round colony transfer surface is fabricated using a diameter measurement ⅛"-¼" smaller than the supporting base so that the transfer surface cannot reach the meniscus of the culture medium. This second design, however, allows a greater surface area of contact between the inner wall of the dish and the side of the transfer pad than does the bumper design described above.

Marking Element

In replica-plating groups of colonies and monitoring subsequent growth of individual colonies on serial replicas, it is desirable and often necessary to place a replica-orienting reference mark on the culture dish and on the replicating device.

These marks, usually made with waterproof ink, allow the laboratory worker to orient or align the replicating device with the culture plate for consistent printing. Thus, corresponding colonies in separate culture dishes can be later "matched-up" and compared for extent of cell growth following incubation.

Omissions and inaccuracies in placing and aligning reference marks for colony printing are quite common, making subsequent comparison of colonies on a series of replicas more difficult. Recognizing these problems and the inconvenience of the manual marking procedure, an automatic means for reference marking cell culture dishes has been introduced within the device of the present invention. The marking means preferably leaves a reference mark or physical impression on the cell culture surface, typically a gel surface such as agar. A simple inexpensive and effective configuration of this marking element in the device consists of a protruding short fin placed on or near the sidewall of the device and extending outward, perpendicular to the sidewall.

In another configuration the marking element consists of a small hollow cylindrical element similarly positioned. The marking element protrudes approximately 1/16"-⅛" above the cell transfer surface assuring that when a culture medium surface, such as gelled agar, is contacted by the transfer surface of the device, an easily visible permanent impression (reference mark) is left in the agar. The marking element may be constructed in a manner which allows it to be pushed by a colony surface toward the colony transfer surface, or so that it may be readily removed if not required. Such removal is preferred when transfer is to a rigid surface rather than a readily pierced surface. For example, the marking element may include a serrated region which when compressed allows the element to be shortened.

Other marking elements may also be configured and positioned within the device of the present invention. These include small marking pens or other instruments leaving a mark, impression or other positional indication on the culture dish or on the culture medium. One or more marking elements described herein are preferably positioned at or near the outside of the replica-plating device to optimize alignment accuracy for multiple replicated culture dishes, while not disrupting the interior field of replicated colonies. In this regard, one of the exterior bumper guards 28 discussed above is extended to protrude above the cell transfer surface. This guard thus has the dual function of being a bumper guard and a marking instrument. This automatic marking allows the replica plating process to be carried out more rapidly, and subsequent alignment of the colonies to be more easily performed.

Adhesive Tab

A double-faced adhesive strip (typically with a peelable paper or plastic backing) is positioned on the back of the replica-plating device to allow securing and immobilizing the pad on a laboratory bench. In this configuration the colony transfer surface is oriented upward. Thus a culture dish about to be contacted by the transfer device is inverted and lowered onto the transfer surface. The laboratory worker can therefore visually monitor physical contact between the colonies on the growth medium surface and the device's transfer surface (because the dish and nutrient medium are generally transparent). Such visual monitoring allows the laboratory worker to control hand pressure on the dish to optimize contact between the dish medium, surface and the transfer device. Without the adhesive strip to anchor the transfer device to the bench the device tends to adhere to the nutrient surface and lift from the bench or move laterally as the dish is removed. Such movement interferes with the replica plating process and results in decreased accuracy of colony transfers. In addition, provision of such a tab allows the user to use only one hand to perform the replica plating action, and will also allow automation of the procedure. It also allows a much thinner device to be produced than has heretofore been possible, because prior devices had to have sufficient depth or thickness to be grasped by a user's fingers or hand and moved in and out of a culture dish.

Use

In the preferred method of use of the device of this invention, a substantially flat transparent culturing medium in a transparent dish is inverted onto the flat replica plating pad (pile material facing upward) to make a master plate imprint. Prior to this contact, the device is firmly anchored to the bench or other work surface by use of the adhesive backing. During this and subsequent contacts with culturing medium in serial replica plating, it is immediately apparent to the eye if an area of agar (such as near the meniscus edge) is not making contact with the transfer surface of the device. A slight shift in finger pressure towards that area of the dish not making contact with the pad always suffices to establish contact. The rapid moisture absorption and substantial moisture capacity of the device assures that if any additional liquid is expressed from the agar surface during the period of re directed pressure, it will be immediately absorbed. The spacing means located on the side wall of the device functions to separate the device from the inside wall of the culture dish as soon as a small overlap is established between the two. The marking bumper guard creates a permanent mark in the culturing surfaces at a fixed position relative to colonies being transferred.

Other embodiments are within the following claims.

I claim:

1. A device for replica plating of living cells, comprising:
a rigid base having a side wall connecting a first upper surface and a first lower surface, and a water absorbing fabric free from dye and preservatives having a second upper surface and a second lower surface, said second lower surface being fixedly bonded to said first upper surface to prevent any horizontal or vertical movement of said fabric; wherein said base comprises an adhesive tab positioned on said first lower surface, and tab being configured and arranged to fixedly secure said base to a flat surface and thereby fixedly secure said fabric in a position raised above said flat surface and accessible for replica plating of said cells, wherein said base comprises a set of bumper guards positioned between said first upper surface and said first lower surface on the side wall of said base, and guards being configured and arranged to prevent contact of said fabric with an inside wall of a culture dish or other container containing said cells.

2. The device of claim 1, further comprising a water absorbing material positioned between a fixedly bonded to said first upper surface and said second lower surface.

3. The device of claim 1, wherein said fabric is a pile material.

4. The device of claim 3, wherein said pile material is loom stage woven 100% cotton pile fabric.

5. The device of claim 1, wherein said bumper guards comprise at least three ridges projecting from the side wall of said base.

6. The device of claim 1, wherein said base is cylindrically shaped.

7. The device of claim 6, wherein said fabric covers said first upper surface and does not extend past the outer circumference of said first upper surface.

8. The device of claim 1, wherein said base comprises biodegradable plastic.

9. The device of claim 2, wherein said water absorbing material is filter paper.

10. The device of claim 1, comprising a removable cover removably positioned over said fabric to maintain the sterility of said fabric.

11. The device of claim 1, comprising an integral marking means said integral marking means extending upward from the outer circumference of said first upper surface, said marking means providing a permanent mark on a solid medium in a cell culture dish when said medium is contacted with said device during use for replica plating of the cells.

12. A device for replica plating of living cells, comprising:
a rigid base having a side wall connecting a first upper surface and a first lower surface, and a water absorbing loom stage woven pile fabric free from dye and preservatives having a second upper surface and a second lower surface, said second lower surface being fixedly bonded to said first upper surface to prevent any horizontal or vertical movement of said fabric, wherein said base comprises a set of bumper guards positioned between said first upper surface and said first lower surface on the side wall of said base, said guards being configured and arranged to prevent contact of said brick with an inside wall of a culture dish or other container containing said cells.

13. A device for replica plating of living cells, comprising:
a base having a side wall connecting a first upper surface and a first lower surface, and a water absorbing layer free from dye and preservatives having a second upper surface and a second lower surface, said second lower surface being fixedly bonded to said first upper surface to prevent any horizontal or vertical movement of said layer, wherein said base comprises an integral marking means configured and arranged to leave a permanent reference mark on a solid medium in a cell culture dish when said medium is contacted with said device during use for replica plating of the cells, said integral marking means extending upward from an outer circumference of said first upper surface.

14. The device of claim 13, comprising a set of bumper guards positioned between said first upper surface and said first lower surface on the side wall of said base, said guards being configured and arranged to prevent contact of said layer with the inside wall of a culture dish or other container containing said cells.

15. The device of claim 14 wherein said marking means is a portion of one of said bumper guards.

16. The device of claim 13 or 14 wherein said marking means is a elongated solid material extending above said second upper surface.

17. A device for replica plating of living cells, comprising:
a rigid base having a side wall connecting a first upper surface and a first lower surface, and a water absorbing fabric having a second upper surface and a second lower surface, said second lower surface being fixedly bonded to said first upper surface in a manner which prevents any horizontal or vertical movement of said fabric; wherein said base comprises an adhesive tab positioned on said first lower surface, said tab being configured and arranged to fixedly secure said base to a flat surface and thereby fixedly secure said fabric in a position raised above said flat surface and accessible for replica plating of said cells, comprising an integral marking means, said marking means providing a permanent mark on a cell culture dish or a solid nutrient medium contacted with said device during use for replica plating of the cells.

18. A device for replica plating of living cells comprising:
   a base having a water absorbing fabric disposed thereon, wherein said base comprises a set of bumper guards positioned at the side of said base, said guards being configured and arranged to prevent contact of said fabric with the inside wall of a culture dish or other container containing said cells.

19. A device for replica plating of living cells, comprising:
   a base having a water absorbing fabric disposed thereon, comprising an integral marking means extending upward from the outer circumference of said base, said marking means providing a permanent mark on a solid medium in a cell culture dish when said medium is contacted with said device during use for replica plating of the cells.

20. The device of claim 18 or 19 wherein said fabric is a loom stage woven pile fabric.

21. The device of claim 19 wherein said base comprises a set of bumper guards positioned at the side of said base, said guards being configured and arranged to prevent contact of said fabric with the inside wall of a culture dish or other container containing said cells.

22. A method for replica plating of living cells, comprising the steps of:
   a) providing a device for replica plating of the cells, comprising a rigid base having a side wall connecting a first upper surface and a first lower surface, and a water absorbing fabric free from dye and preservatives having a second upper surface and a second lower surface, said second lower surface being fixedly bonded to said first upper surface to prevent any horizontal or vertical movement of said fabric; wherein said base comprises an adhesive tab positioned on said first lower surface, said tab being configured and arranged to fixedly secure said base to a flat surface and thereby fixedly secure said fabric in a position raised above said flat surface and accessible for replica plating of said cells, wherein said base comprises a set of bumper guards positioned between said first upper surface and said first lower surface on the side wall of said base, said guards being configured and arranged to prevent contact of said fabric with the inside wall of a culture dish or other container containing said cells;
   b) positioning said device on a flat surface with said tab fixedly secured to said flat surface,
   c) placing the cells in contact with said second upper surface to cause the cells to be transferred to said second upper surface, and
   d) subsequently placing a solid medium cellular receiving surface in contact with said second upper surface to cause the cells to be transferred to said receiving surface.

23. A method for replica plating of living cells, comprising the steps of:
   a) providing a device for replica plating of the cells, comprising a rigid base having a side wall connecting a first upper surface and a first lower surface, and a water absorbing loom stage woven pile fabric free from dye and preservatives having a second upper surface and a second lower surface, said second lower surface being fixedly bonded to said first upper surface to prevent any horizontal or vertical movement of said fabric, wherein said base comprises a set of bumper guards positioned between said first upper surface and said first lower surface on the side wall of said base, said guards being configured and arranged to prevent contact of said fabric with the inside wall of a culture dish or other container containing said cells;
   b) placing the cells in contact with said second upper surface to cause the cells to be transferred to said second upper surface, and
   c) subsequently placing a solid medium cellular receiving surface in contact with said second upper surface to cause the cells to be transferred to said receiving surface.

24. A method for replica plating of living cells, comprising the steps of:
   a) providing a device for replica plating of the cells, comprising a base having a side wall connecting a first upper surface and a first lower surface, and a water absorbing layer free from dye and preservatives having a second upper surface and a second lower surface, said second lower surface being fixedly bonded to said first upper surface to prevent any horizontal or vertical movement of said fabric, wherein said base comprises an integral marking means configured and arranged to leave a permanent reference mark on a cell culture dish or a solid nutrient medium contacted with said device during use for replica plating of the cells, said integral marking means extending upward from the outer circumference of said first upper surface,
   b) placing the cells in contact with said second upper surface to cause the cells to be transferred to said second upper surface, and simultaneously causing a reference mark to be placed on said cell culture dish or said solid nutrient medium, and
   c) subsequently placing a solid medium cellular receiving surface in contact with said second upper surface to cause the cells to be transferred to said receiving surface and a second reference mark to be simultaneously placed in said cellular receiving surface.

25. A method for replica plating of living cells, comprising the steps of:
   (a) providing a device for replica plating of living cells comprising:
   a base having a water absorbing fabric disposed thereon, wherein said base comprises a set of bumper guards positioned at the side of said base, said guards being configured and arranged to prevent contact of said fabric with the inside wall of a culture dish or other container containing said cells;
   (b) placing the cells in contact with said fabric to cause the cells to be transferred to said fabric, and
   (c) subsequently placing a solid medium cellular receiving surface in contact with the fabric to cause the cells to be transferred to said surface.

26. A method for replica plating of living cells, comprising the steps of:
   (a) providing a device for replica plating of living cells comprising:
   a base having a water absorbing fabric disposed thereon, wherein said base comprises a set of bumper guards positioned at the side of said base, said guards being configured and arranged to prevent contact of said fabric with the inside wall of a culture dish or other container containing said cells;
   (b) placing the cells in contact with said fabric to cause the cells to be transferred to said fabric, and
   (c) subsequently placing a solid medium cellular receiving surface in contact with the fabric to cause the cells to be transferred to said surface.

* * * * *

UNITED STATES PATENT AND TRADEMARK OFFICE
CERTIFICATE OF CORRECTION

PATENT NO. : 5,061,621

DATED : October 29, 1991

INVENTOR(S) : Daniel Perlman

It is certified that error appears in the above-identified patent and that said Letters Patent is hereby corrected as shown below:

Col. 2, ln. 2:

delete "phase", replace with --phage--

Col. 6, ln. 30:

insert -- . -- between the words "growth" and "One"

Col. 7, ln. 27-33:

delete [Bold] print

Col. 8, ln. 61:

insert -- ' -- between the "r" and "s" in "user s"

UNITED STATES PATENT AND TRADEMARK OFFICE
CERTIFICATE OF CORRECTION

PATENT NO. : 5,061,621

DATED : October 29, 1991

INVENTOR(S) : Daniel Perlman

It is certified that error appears in the above-identified patent and that said Letters Patent is hereby corrected as shown below:

Col. 9, ln. 13:

insert -- - -- between the "e" and "d" in "re directed"

Col. 9, ln. 33:

delete "and", replace with --said--

Col. 10, ln. 18:

delete "brick", replace with --fabric--

Signed and Sealed this

Third Day of August, 1993

Attest:

MICHAEL K. KIRK

*Attesting Officer*      *Acting Commissioner of Patents and Trademarks*